US00PP18743P2

(12) United States Plant Patent
Oudshoorn

(10) Patent No.: US PP18,743 P2
(45) Date of Patent: Apr. 22, 2008

(54) ***VERONICA* PLANT NAMED 'PINK EVELINE'**

(50) Latin Name: *Veronica longifolia*
Varietal Denomination: Pink Eveline

(75) Inventor: Hubertus Gerardus Oudshoorn, Rijpwetering (NL)

(73) Assignee: Future Plants Licentie B.V., Lisserbroek (NL)

( * ) Notice: Subject to any disclaimer, the term of this patent is extended or adjusted under 35 U.S.C. 154(b) by 0 days.

(21) Appl. No.: 11/637,854

(22) Filed: Dec. 12, 2006

(51) Int. Cl.
*A01H 5/00* (2006.01)

(52) U.S. Cl. ..... Plt./251

(58) Field of Classification Search ..... Plt./251
See application file for complete search history.

*Primary Examiner*—Kent Bell
(74) *Attorney, Agent, or Firm*—C. A. Whealy

(57) ABSTRACT

A new and distinct cultivar of *Veronica* plant named 'Pink Eveline', characterized by its upright plant habit; freely flowering habit; dark pink-colored flowers; and good garden performance.

2 Drawing Sheets

Botanical designation: *Veronica longifolia.*
Cultivar denomination: 'Pink Eveline'.

BACKGROUND OF THE INVENTION

The present invention relates to a new and distinct cultivar of *Veronica,* botanically known as *Veronica longifolia* and hereinafter referred to by the name 'Pink Eveline'.

The new *Veronica* is a product of a planned breeding program conducted by the Inventor in Rijpwetering, The Netherlands. The objective of the breeding program is to create new *Veronica* cultivars with numerous attractive flowers and good garden performance.

The new *Veronica* is a naturally-occurring branch mutation of the *Veronica longifolia* cultivar Eveline, disclosed in U.S. Plant Pat. No. 14,888. The new *Veronica* was discovered by the Inventor within a population of plants of 'Eveline' grown in a controlled environment in Rijpwetering, The Netherlands in 2005.

Asexual reproduction of the new cultivar by vegetative cuttings in Rijpwetering, The Netherlands, since 2005, has shown that the unique features of this new *Veronica* are stable and reproduced true to type in successive generations.

SUMMARY OF THE INVENTION

Plants of the cultivar Pink Eveline have not been observed under all possible environmental conditions. The phenotype may vary somewhat with variations in environment such as temperature and light intensity without, however, any variance in genotype.

The following traits have been repeatedly observed and are determined to be the unique characteristics of 'Pink Eveline'. These characteristics in combination distinguish 'Pink Eveline' as a new and distinct cultivar:

1. Upright plant habit.
2. Freely flowering habit.
3. Dark pink-colored flowers.
4. Good garden performance.

Plants of the new *Veronica* differ from plants of the parent, the cultivar Eveline, primarily in flower color as plants of the cultivar Eveline have violet-colored flowers.

Plants of the new *Veronica* can be compared to plants of the cultivar Pink Panther, disclosed in U.S. Plant Pat. No. 16,311. In side-by-side comparisons conducted by the Inventor in Rijpwetering, The Netherlands, plants of the new *Veronica* differed from plants of the cultivar Pink Panther in the following characteristics:

1. Plants of the new *Veronica* had smaller leaves than plants of the cultivar Pink Panther.
2. Plants of the new *Veronica* and the cultivar Pink Panther differed in flower color.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Veronica.*

The photograph on the first sheet comprises a side perspective view of a typical flowering plant of 'Pink Eveline' grown in a container.

The photograph at the top of the second sheet is a close-up view of a typical inflorescence of 'Pink Eveline'.

The photograph at the bottom of the second sheet is a close-up view of a typical leaf of 'Pink Eveline'.

DETAILED BOTANICAL DESCRIPTION

In the following description, color references are made to The Royal Horticultural Society Colour Chart, 2001 Edition, except where general terms of ordinary dictionary significance are used. Plants used for the aforementioned photographs and following description were grown under conditions which closely approximate commercial production conditions during the spring and summer in an outdoor nursery in Rijpwetering, The Netherlands for about one year. During the production of the plants, day temperatures ranged from 14° C. to 32° C. and night temperatures ranged from 8° C. to averaged 18° C.

Botanical classification: *Veronica longifolia* cultivar Pink Eveline.

Parentage: Naturally-occurring branch mutation of the *Veronica longifolia* cultivar Eveline, disclosed in U.S. Plant Pat. No. 14,888.

Propagation:

*Type cutting.*—Vegetative cuttings.

*Time to initiate roots.*—About 20 to 30 days at 20° C.

*Time to produce a rooted young plant.*—About 60 to 70 days at 20° C.

*Root description.*—Fine; tan in color.

*Rooting habit.*—Freely branching; moderately dense.

Plant description:

*Form.*—Upright plant form; narrow inverted triangle. Freely basal branching with about five main stems; moderately vigorous growth habit.

*Plant height.*—About 38.5 cm.

*Plant width.*—About 19.5 cm.

*Lateral branch description.*—Length: About 11.6 cm. Diameter: About 2 mm. Internode length: About 2.3 cm. Strength: Strong. Texture: Densely pubescent. Color: 144B to 144C.

Foliage description:

*Arrangement.*—Opposite, simple.

*Length.*—About 4 cm.

*Width.*—About 1.4 cm.

*Shape.*—Narrowly ovate to lanceolate.

*Apex.*—Acute.

*Base.*—Attenuate.

*Margin.*—Serrate.

*Texture, upper and lower surfaces.*—Sparsely pubescent.

*Venation pattern.*—Pinnate.

*Color.*—Developing foliage, upper surface: Slightly darker than 143A. Developing foliage, lower surface: 137D. Fully expanded foliage, upper surface: Slightly darker than 137A; venation, 144B. Fully expanded foliage, lower surface: 137B; venation, 144B to 144C.

*Petiole length.*—About 6 mm.

*Petiole diameter.*—About 1.5 mm.

*Petiole texture, upper and lower surfaces.*—Sparsely pubescent.

*Petiole color, upper and lower surfaces.*—144A to 144B.

Flower description:

*Flower arrangement and shape.*—Single campanulate flowers arranged on terminal racemes; flowers face mostly outwardly. Freely flowering, about 100 flowers per inflorescence.

*Fragrance.*—None detected.

*Natural flowering season.*—Flowering continuous from July through September in The Netherlands.

*Flower longevity on the plant.*—About one week; flowers not persistent.

*Flower buds.*—Length: About 6 mm. Diameter: About 1.5 mm. Shape: Narrowly ovate. Color: 63B.

*Inflorescence size.*—Length: About 14 cm. Diameter: About 2.1 cm.

*Flowers.*—Diameter: About 7 mm. Depth (height): About 1 cm.

*Petals.*—Arrangement: Four, fused halfway to base. Length: About 8 mm. Width: About 3 mm. Shape: Oblanceolate. Apex: Broadly acute. Margin: Entire. Texture, upper and lower surfaces: Smooth, glabrous. Color: When opening and fully opened, upper surface: 64C; towards the apex, 65A; color becoming closer to 64B with development. When opening and fully opened, lower surface: 64C; towards the apex, slightly lighter than 64C.

*Calyx.*—Shape: Four sepals fused into a tube; apices, acute. Length: About 4 mm. Width: About 2 mm. Texture, upper and lower surfaces: Smooth, glabrous. Color, upper and lower surfaces: 137C.

*Peduncles.*—Strength: Strong. Length: About 14 cm. Diameter: About 1.5 mm. Aspect: Mostly upright. Texture: Smooth, glabrous. Color: 144B to 144C.

*Pedicels.*—Strength: Strong. Length: About 2 mm. Diameter: About 0.5 mm. Aspect: About 45° from the stem axis. Texture: Smooth, glabrous. Color: 144B to 144C.

*Reproductive organs.*—Stamens: Quantity per flower: Two. Filament length: About 6 mm. Filament color: 77B to 77C. Anther shape: Elliptic. Anther length: About 2 mm. Anther color: 77A to 77B. Pollen amount: Scarce. Pollen color: 156D. Pistils: Quantity per flower: One. Pistil length: About 5 mm. Stigma shape: Clavate; flattened. Stigma color: 77A. Style length: About 4.5 mm. Style color: 77A. Ovary color: 144C to 144D.

*Seed/fruit.*—Seed and fruit production has not been observed.

Disease/pest resistance: Plants of the new *Veronica* have not been noted to be resistant to pathogens and pests common to *Veronica*.

Garden performance: Plants of the new *Veronica* have exhibited good tolerance to rain and wind and have been observed to tolerate temperatures ranging from USDA Hardiness Zones 4 to 9.

It is claimed:

1. A new and distinct *Veronica* plant named 'Pink Eveline' as illustrated and described.

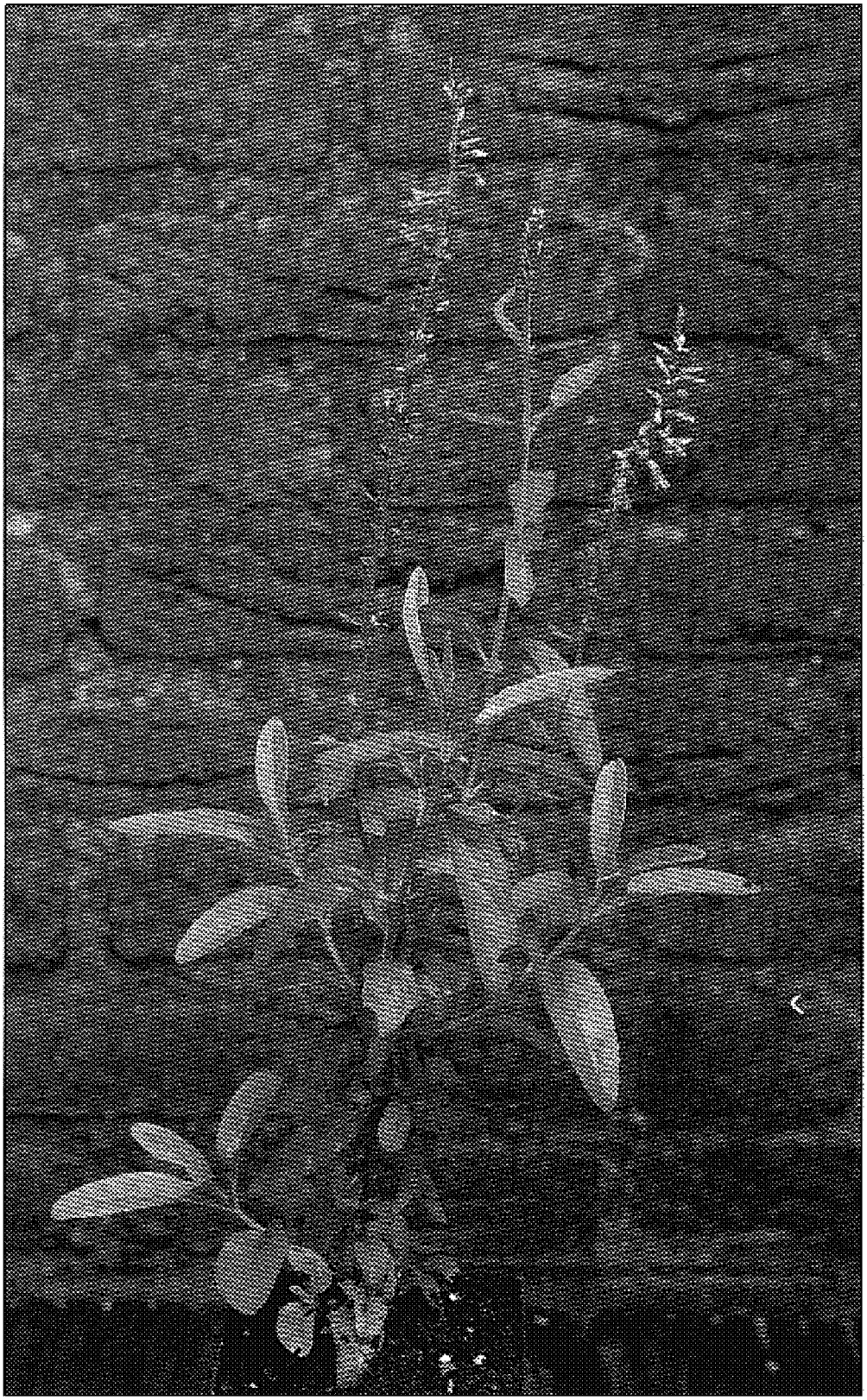

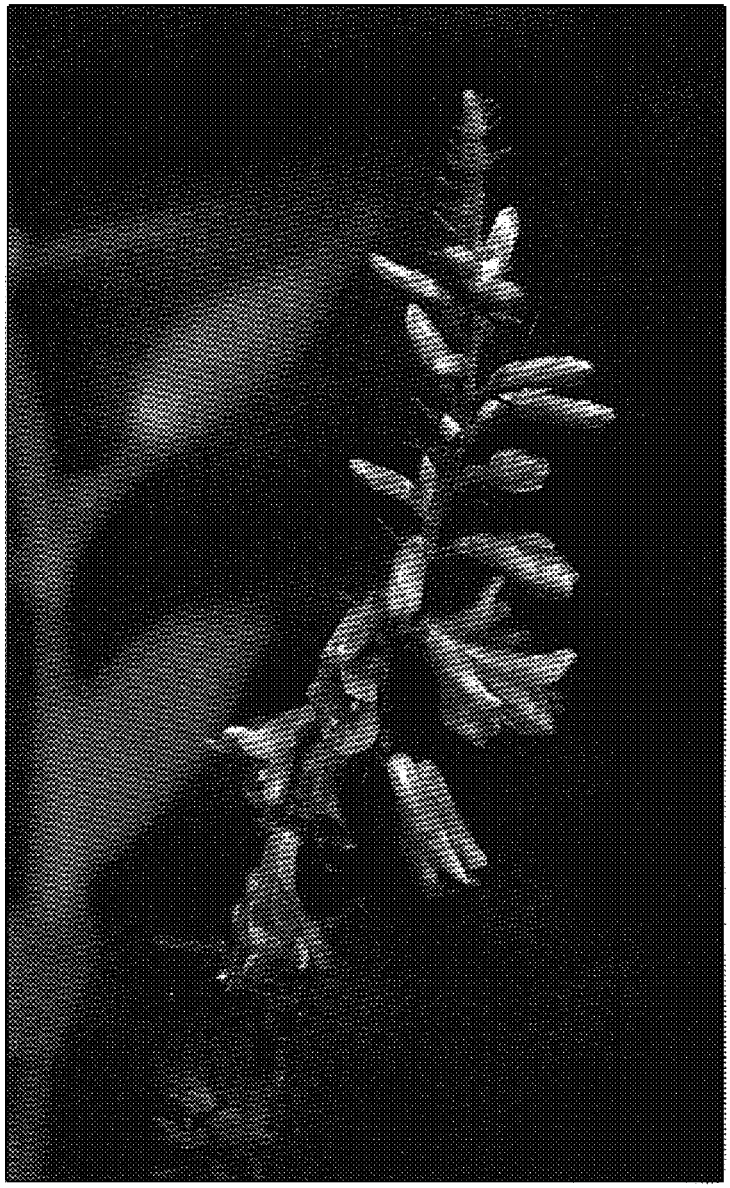
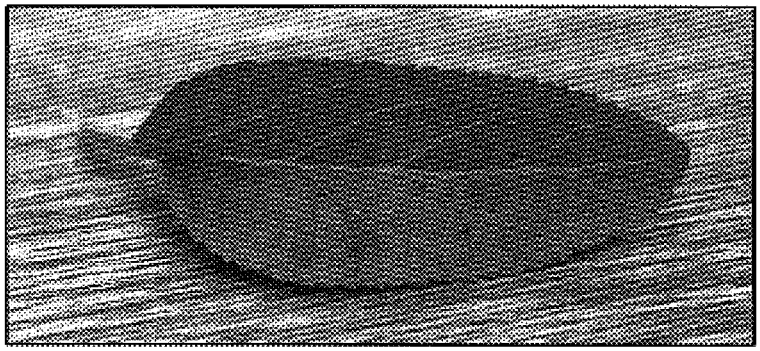

* * * * *